United States Patent [19]
Jones et al.

[11] Patent Number: 5,557,008
[45] Date of Patent: Sep. 17, 1996

[54] PROCESS FOR THE INTRODUCTION OF FLUORO SUBSTITUENTS

[75] Inventors: Craig W. Jones; William R. Sanderson; John P. Sankey, all of Warrington, United Kingdom

[73] Assignee: Solvay Interox Limited, Warrington, England

[21] Appl. No.: 524,252

[22] Filed: Sep. 6, 1995

[30] Foreign Application Priority Data

Sep. 10, 1994 [GB] United Kingdom .................... 9418305

[51] Int. Cl.$^6$ ................................. C07C 17/013
[52] U.S. Cl. ............................ 560/145; 560/131; 568/56; 570/142
[58] Field of Search ................................. 560/131, 145; 568/56; 570/142

[56] References Cited

U.S. PATENT DOCUMENTS

| | | | |
|---|---|---|---|
| 3,461,155 | 8/1969 | Rice | 260/479 |
| 4,631,151 | 12/1986 | Kobayashi et al. | 260/408 |
| 5,475,165 | 12/1995 | Palmer et al. | 570/144 |

FOREIGN PATENT DOCUMENTS

| | | |
|---|---|---|
| 0155093A2 | 9/1985 | European Pat. Off. . |
| 2062832 | 3/1990 | Japan ..................... 570/142 |

OTHER PUBLICATIONS

J. Org. Chem. 1988, 53, 3321–3325, "Oxiranes from Methnylenation of the Ester Carbonyl Group by Diazomethane", Strazzolini et al.

J. Am. Chem. Soc., vol. 84, pp. 3661–3666 (1962), "Addition of $CF_3$ Radicals to Aromatic Hydrocarbons", Stefani et al.

J. Org. Chem. 1986, 51, 1365–1367, "Cobalt (III)–Catalyzed Trifluoroacetoxylation of Benzene", DiCosimo et al.

J. Org. Chem., vol. 53, No. 19, 1988, "Direct Perfluoroalkylation Including Trifluoromethylation of Aromatics with Perfluoro Carboxylic Acids Mediated by Xenon Difluoride", Tanabe et al., pp. 4582–4585.

J. Chem. Soc., Chem. Commun., 1987, "Perfluoroakylation of Anilines in the Presence of Zinc and Sulphur Dioxide", Wakselman et al., pp. 1700–1703.

J. Chem. Soc., Perkin Trans. 1989, "Perfluoroalkylations of Nitrogen–Containing Heteroaromatic Compounds with Bis(perfluoroalkanoyl) Peroxides", Yoshida et al., pp. 909–915.

Electrochimica Acta, 1976, vol. 21, pp. 987–989, "Electro–Organic Reactions–VIII. The Methylation and Trifluoromethylation of Pyridine By Anodically Generated Radicals", Utley et al., pp. 987–989.

Bull. Chem. Soc. Jpn. 61, 3531–3537 (1988), "Photochemical Trifluoromethylation of Some Aromatic and Heteroaromatic Compounds with Trifluoromethyl Bromide", Akiyama et al.

Journal of Fluorine Chemistry, 5 (1975) 245–263, "A Novel Telomerization Procedure for Controlled Introduction of Perfluoro–n–Alkyl End Groups", Gumprecht et al.

Journal of Fluorine Chemistry, 32 (1986) 467–470, "Flash Theromlysis of Aryl Trifluoroacetates: A New Approach to Trifluoromethylated Aromatic Compounds", Kobayashi et al.

Journal of Fluorine Chemistry, 46 (1990) 423–431, "Trifluoromethylation Aromatic Compounds with Bis(Trifluoroacetyl) Peroxide", Sawada et al.

Journal of Fluorine Chemistry, 57 (1992) 209–217, "Perfluoroalkylation of Azo Compounds", Matsui et al.

Polymer Journal, vol. 22, No. 7, pp. 623–627 (1990), "Syntheses of Perfluoroalkylated Styrene Monomers with Bis(perfluoroalkanoyl) Peroxides", Mitani et al.

J. Org. Chem. 1983, 48, 4908–4910, "Electron–Transfer Reactions Between Perfluoroacyl Peroxides and Methoxybenzenes", Zhao et al.

JCS Perkin II, 1975, pp. 435–439, "Reactions of Trifluoromethyl Radicals. Part I. The Photochemical Reactions of Trifluoroiodomethane with Benzene and Some Halogenobenzenes", Birchall et al.

J. Chem. Soc. Perkin, Trans. 1 (1990), "Reactions of Trifluoromethyol Bromide and Related Halides: Part 10. Perfluoroalkylation of Aromatic Compounds Induced by Sulphur Dioxide Radical Anion Precursors", Tordeux et al. 2293–2299.

Journal of Fluorine Chemistry, 47 (1990) 283–299, "Trifluormethylierungs–Reaktionen von Te $(CF_3)_2$ Mit Halogenbenzolen und Methylbenolen", Naumann et al.

Tetrahedron Letters, vol. 23, No. 38, pp. 3929–3930 (1982), "N–Trifluoromethyl–N–Nitrosobenzenesulfonamide. A New Trifluoromethylating Agent", Umemoto et al.

Reviews on Heteroatom Chemistry, vol. 8, pp. 205–231, "Fluorinated Organic Peroxides–Their Decomposition Behavior and Applications", Sawada, 1993.

Derwent Publications Ltd., 89–312808/43, Sep. 14, 1989, Nippon Oils & Fats KK JP 1–230564A.

Derwent Publications Ltd., 89–314107/43, Sep. 19, 1989, Nippon Oils & Fats KK JP 1–2332431A.

Derwent Publications, 92–145345/18, Mar. 16, 1992, Nippon Oils & Fats KK JP 4–082860A.

Derwent Publications, 93–024084/03, Dec. 7, 1992, Nippon Oils & Fats Co. Ltd. JP 4–352769A.

*Primary Examiner*—Michael Lusignan
*Assistant Examiner*—Erma Cameron
*Attorney, Agent, or Firm*—Larson and Taylor

[57] ABSTRACT

A one pot process for the perfluoroalkylation and/or perfluoroacyloxylation of organic substrates is provided. The process comprises contacting a substrate with a perfluoroalkanoic anhydride in the presence of an inorganic peroxygen compound at a temperature of greater than 10° C. Substrates that can be perfluoroalkylated and/or perfluoroacyloxylated include alkylbenzenes, halogenated aromatic compounds, alkoxybenzenes, aryl benzenes, and aromatic and aliphatic disulphides. Preferably, the perfluoroalkanoic anhydride is trifluoroacetic anhydride and the inorganic peroxygen compound is sodium percarbonate.

15 Claims, No Drawings

PROCESS FOR THE INTRODUCTION OF FLUORO SUBSTITUENTS

This invention concerns a process for the introduction of fluoro substituents into organic substrates. More specifically, this invention concerns a process for the introduction of perfluoroalkyl groups and/or perfluoroacyloxy groups.

Fluorinated compounds are valued for use in a number of sections of the chemical industry, for example as dyes, polymers, pharmaceuticals and agrochemicals. The presence of a fluorinated substituent often has a significant effect on the properties of the compound, for example, a trifluoromethyl group can significantly alter the properties of biologically active molecules on account of imparting increased lipophilicity and the high electronegativity of the group.

Many different processes and reagents have been proposed for the introduction of fluoro substituents, particularly for perfluoroalkylation. For example, on an industrial scale, trifluoromethylation can be achieved by first trichlorinating a methyl aromatic compound such as toluene, followed by reaction with hydrogen fluoride at high pressure and elevated temperature. The process suffers from numerous disadvantages, including the need for handling the toxic and corrosive gases chlorine and hydrogen fluoride, the need for high pressure apparatus and the fact that the aromatic compound should be free from further alkyl substituents to avoid the production of unwanted chlorinated and fluorinated by-products.

Photochemical processes have been proposed for use with many reagents, including iodotrifluoromethane and bromotrifluoromethane, as for example, in Birchall et al, Perkin Trans, II, 1975, p435 and Akijana, Bull. Chem. Soc. Jpn., 1988, 61, p3531. Both of these reagents suffer from the disadvantage of being gaseous, and are therefore correspondingly difficult to handle. They also often need to be reacted under pressure to achieve acceptable results, which increases the cost of the process. Other reagents that have been proposed include heavy metal bis(trifluoromethyl) compounds such as bis(trifluoromethyl)mercury, and bis(trifluoromethyl)tellurium, for example, in Cech et al, Nucleic Acids Syrup. Serv. 1981, 9, p29 and Naumann, J. Fluorine Chem., 1990, 47, p283. These other reagents suffer from the drawback of leaving toxic heavy metal residues, which are difficult and costly to handle and dispose of. Further reagents include diazofluoromethane and N-trifluoromethyl-N-nitrosulphonamides, as described for example, in Stefani, J. Am. Chem. Soc., 1962, 84, 3661 and Umemeto, Tetrahedron Lett., 1982, 23, 3929. These further reagents suffer from being relatively expensive organic reagents, and are commonly complex to synthesise. Indeed, their preparation commonly involves the use of a gaseous reagent such as iodotrifluoromethane.

Electrochemical processes have been proposed, commonly employing solutions of partially neutralised trifluoroacetic acid, see for example Uttley et al, Electrochim. Acta. 1976, 21, p987. Industrial-scale electrochemical processes commonly suffer from the high cost of the energy involved.

Other methods of trifluoromethylation include the reactions between bromotrifluoromethane and zinc/sulphur dioxide or sodium dithionate, for example those described in Tordeux et al, J. Chem. Soc., Perkin Trans. I, 1990, pp2293. This method has the drawback of involving the handling of gaseous reagents. The reaction between xenon difluoride and trifluoroacetic acid has also been proposed, as for example in Tanabe et al, J. Org. Chem., 1988, 53, 4582, but this method has the disadvantage of using xenon difluoride, a very aggressive fluorinating reagent which sublimes readily and therefore requires handling under vacuum. A further method that has been proposed includes the reaction between trifluoromethane sulphinate and t-butylhydroperoxide, as for example in Wakselman et al, J. Chem. Soc., Chem. Comm., 1987, 1701. Bis(perfluoroacyl) peroxides have also been proposed as reagents for introducing perfluoroalkyl groups into organic substrates, as for example in Yoshida et al, J. Chem. Soc. Perkin. Trans. I, 1989, 909; in Gumprecht et al, J. Fluorine Chemistry, 5 (1975) pp245–263; Zhao et al, J Org Chem 1983, 48, 4808–4910; European patent application No. 0 155 093; Japanese patent application nos. J01230564, J01233231 and JP04352769; Sawada et al, J Fluorine Chemistry, 46 (1990) pp423–431; Mitani et al, Polymer Journal, Vol 22, No. 7 pp623–627 (1990); Matsui et al, J Fluorine Chemistry, 57 (1992) 209–217; and the chapter by Sawada, Reviews on Heteroatom Chemistry, Vol 8, pp205–231 (1993), ed Ohno & Okuyama. In these references, the bis(perfluoroacyl) peroxides are prepared in a first reaction, optionally by reaction between an inorganic peroxygen and a perfluoracyl halide or anhydride. The preparative reaction is carried out at very low temperature, often in the range of from 0° to –10° C., in order to avoid destabilisation of the acyl peroxide. The reaction between the acyl peroxide and the organic substrate is carried out in a second, separate subsequent stage. The second reaction generally employs a temperature significantly higher than that employed for the preparation of the acyl peroxide, commonly 40° to 55° C., although Zhao et al, European patent application no. 0 155 093 and Japanese patent application J01230564 teach that temperatures of 0° C. can be employed. None of these references teach a single stage process for the introduction of a perfluoro substituent into an organic substrate. Indeed, the method of Wakselman and those methods employing bis(trifluoroacetyl) peroxide involve the handling of isolated organic peroxides, with their associated, well recognised, hazardous properties.

The problems associated with the perfluoroalkylation processes of the prior art are generally recognised, see for example, the comments in Kobayashi et al, Journal of Fluorine Chemistry, 1986, 32, p467. It would therefore be desirable to identify an alternative method for the introduction of perfluoroalkyl substituents into organic substrates.

One conventional method of introducing perfluoroacyloxy groups involve the derivatisation of a hydroxy group, for example a phenol, by reaction with a perfluoroacyloxy anhydride or chloride, for example, the method disclosed by Strazzolini et al, J. Org. Chem., 1988, 53, p3321. Such processes have the disadvantage that they are not conveniently applicable to compounds that do not comprise a hydroxyl group, for example alkylaromatic compounds, because of the need to introduce a hydroxyl group in a separate process step. A further method for introducing perfluoroacyloxy groups employs heavy metal catalysts, for example the method disclosed by Dicosimo et al, J. Org. Chem., 1986, 51, pp 1365–7. Such methods suffer from disadvantages resulting from the unfavourable toxicological and environmental properties of heavy metals. Japanese patent application JP 04082860 discloses a method of introducing a perfluoroacyloxy substituent into the side chains of certain organic compounds in which an isolated bis(perfluoroacyl) peroxide is employed. Such a method involves the handling of isolated organic acyl peroxides with their associated and well recognised hazardous properties. It would therefore be desirable to identify an alternative method for the introduction of perfluoroacyloxy substituents into organic substrates.

On account of the problems associated with the prior art processes for introducing perfluorinated substituents into organic substrates, it therefore remains desirable to identify an additional and further process for the introduction of perfluoro substituents into organic substrates.

It is a first object of the present invention to provide an additional process for the introduction of perfluoroalkyl groups and/or perfluoroacyloxy groups into certain organic substrates that avoids or ameliorates one or more of the problems associated with prior art processes, and particularly a single stage process that avoids the need to handle isolated bis(perfluoracyl) peroxides.

It is a second object of certain aspects of the present invention to provide a process for the introduction of perfluorinated substituents into certain organic substrates in which the degree of perfluoroalkylation relative to the degree of perfluoroacyloxylation can be varied by control of the process conditions.

According to one aspect of the present invention, there is provided a one pot process for introducing a perfluorinated substituent into an organic substrate susceptible to electrophilic attack, characterised in that the substrate is free from any heteroatom bonded to a hydrogen atom and is selected from the group consisting of aromatic compounds comprising a hydrogen atom bonded to an aromatic ring and/or at least two concatenated nucleophilic heteroatoms, and aliphatic compounds comprising at least two concatenated nucleophilic heteroatoms, and that the process comprises contacting the substrate with a perfluoroalkanoic anhydride in the presence of an inorganic peroxygen compound at a temperature of greater than 10° C.

The process according to the present invention can be employed for introducing perfluoro substituents into organic aliphatic and aromatic compounds which are susceptible to electrophilic attack and which are free from heteroatoms bonded to a hydrogen atom. When the substrate is an aromatic compound, the substrate comprises at least one hydrogen atom bonded to an aromatic ring and/or at least two concatenated nucleophilic heteroatoms, particularly a disulphide group. It will be recognised that it is preferable for the aromatic compound not to be highly deactivated by the presence of strongly electron withdrawing groups, such as nitro groups bonded thereto. Without wishing to be bound by any theory, it is believed that the process according to the present invention proceeds via the in situ generation of the perfluoroacyl peroxide radicals with the subsequent formation of radical cations from the substrate. Advantageously, the process according to the present invention provides a single stage or one pot process for the introduction of perfluorinated substituents. The fact that such a process can successfully be carried out is surprising, given the low concentrations of any peroxide radicals that would be formed, the poor stability of such radicals and the possibility of competing reaction between the organic substrate and the source of inorganic peroxygen. The skilled man will expect to apply the process of the instant invention to a range of aromatic substrates similar to those employable in all other processes employing the perfluoroacyl peroxide radical, such as the method disclosed by Yoshida et al discussed above.

The process according to the present invention has in many embodiments been found to be particularly applicable to aromatic substrates having a vapour phase Ionisation Potential measured by the method of Moore, "Ionisation potentials and Ionisation Limits derived from Analysis of Optical Spectra", Stand. Ref. Data Ser., Nat. Bur. Stand. (US) No. 34, 1970 of less than 9.5 electron volts, preferably less than 9 electron volts. Aromatic substrates having an ionisation potential of 9.5 or more can also be employed, although lower yields may result. Examples of aromatic substrates include alkyl substituted aromatic compounds such as alkylbenzenes, particularly toluene, xylene, ethylbenzene; halogen substituted aromatic compounds, particularly chloro and bromobenzene; aryl substituted aromatic compounds particularly biphenyl; alkoxy substituted aromatic compounds such as alkoxybenzenes particularly anisole, aromatic ketones including benzophenone and acetophenone, poly aromatic ring compounds such as naphthalene and phenantharene; azo compounds including azobenzenes; heteroaromatics including tetrahydrofuran, tetrahydrothiophene and acridine; aromatic disulphides such as diphenyldisulphide, 2,2'-dithiodipyridine and benzodithiols, particularly 3H-1,2-benzodithiol-3-one; and aromatic sulphides including benzothiazoles. When the substrate is an aliphatic compound, the substrate comprises at least two concatenated nucleophilic heteroatoms, particularly a disulphide group. Examples of aliphatic substrates include alkyl disulphides such as dipropyl and dibutyl disulphide and thioctic acid.

Inorganic peroxygen compounds that can be employed in the process according to the present invention include inorganic persalts such as sodium percarbonate, sodium perborate mono and tetrahydrates, metal peroxides such as calcium peroxide and persulphate salts such as potassium monopersulphate. A further inorganic peroxygen compound comprises aqueous hydrogen peroxide solutions, including mixtures of aqueous hydrogen peroxide solutions with inorganic salts such as sodium carbonate or borax. It will be recognised that perfluoroalkanoic anhydrides can be hydrolysed by water, and thus excess water can impair the efficiency of the process according to the present invention. When aqueous hydrogen peroxide solutions are employed, it is therefore desirable that the solutions should be concentrated solutions, often comprising at least 65% by weight hydrogen peroxide, and preferably at least 80% by weight, to reduce the amount of water introduced. The term inorganic peroxygen compounds herein also includes sources of inorganic peroxygens, for example hydrogen peroxide adducts such as urea-hydrogen peroxide, triphenylphosphine oxide-hydrogen peroxide and amine oxide-hydrogen peroxide adducts.

It will be recognised that the nature of the substrate and the nature of the inorganic peroxygen compound, in addition to the conditions employed, will influence the nature and extent of the introduction of perfluoro substituents achieved by the process according to the present invention. This represents an advantage for the process of the present invention, because by careful selection of the appropriate substrate and conditions, the skilled man can direct particularly the nature of the introduction of perfluoro substituents that takes place. For example, when the substrate is an aromatic or aliphatic disulphide it is believed that the perfluorinated product is preferentially the product from cleavage of the disulphide bond followed by perfluoroalkylation of the sulphur atom.

When the substrate is an aromatic compound other than a disulphide, the nature of the perfluoro substitution is dependent upon the process temperature and the inorganic peroxygen employed. At temperatures at the lower end of the temperature range for the instant process, such as from 10° to 35° C., generally a greater proportion of perfluoroacyloxylation and a lower proportion of perfluoroalkylation occurs compared with process temperatures at the higher end of the temperature range, such as greater than 40° C., particularly from 45° C. to 80° C.

At a temperature towards the higher end of the temperature range, the selection as inorganic peroxygen compound of calcium peroxide or a mixture of aqueous hydrogen peroxide and sodium carbonate has been found to favour more selective perfluoroacetoxylation, whereas the selection as inorganic peroxygen of sodium perborate tetrahydrate or aqueous hydrogen peroxide solution has been found to favour more selective perfluoroalkylation. Selection of sodium percarbonate as the inorganic peroxygen has been found to favour more selective perfluoroacetoxylation at temperatures towards the lower end of the temperature range, but to favour more selective perfluoroalkylation at the higher end of the temperature range.

According to a further aspect of the present invention, there is provided a one pot process for the perfluoroalkylation of an organic substrate susceptible to electrophilic attack, characterised in that the substrate is free from any heteroatom bonded to a hydrogen atom and is selected from the group consisting of aromatic compounds comprising a hydrogen atom bonded to an aromatic ring and/or at least two concatenated nucleophilic heteroatoms, and aliphatic compounds comprising at least two concatenated nucleophilic heteroatoms, and that the process comprises contacting the substrate with a perfluoroalkanoic anhydride in the presence of sodium percarbonate at a temperature greater than 45° C.

Fluoroalkanoic anhydrides that can be employed in the process according to the present invention include perfluoroalkanoic anhydrides, particularly trifluoroacetic anhydride, perfluoropropionic anhydride, perfluorobutanoic anhydride, perfluoropentanoic anhydride, perfluorohexanoic anhydride and perfluoroheptanoic anhydride, Preferably, the perfluoroalkanoic anhydride is trifluoroacetic anhydride.

The mole ratio of perfluoroalkanoic anhydride to inorganic peroxide is commonly selected to be greater than 1:1, and is usually less than 15:1, with ratios in the range of from 2:1 to 10:1 being preferred.

In many embodiments of the present invention, the substrate serves as solvent. However, the process according to the present invention can be carried out in the presence of an additional solvent if desired. On account of the postulated involvement of radicals in the mechanism discussed above, it is desirable that any additional solvent employed should be resistant to attack by radicals. Examples of suitable additional solvents include chlorofluorocarbons, but t he use of chlorofluorocarbons is often not favoured on account of their poor environmental properties.

When an additional solvent is employed, the relative amounts of substrate to inorganic peroxide is commonly selected to be such that mole ratio of substrate to available oxygen is the range of from 1:1 to 6:1, often 2:1 to 4:1. When the substrate serves as solvent, the relative amounts of substrate to inorganic peroxide is commonly selected to be such that mole ratio of substrate to available oxygen is the range of from 10:1 to 50:1, often 12:1 to 30:1, and preferably 15:1 to 25:1.

In the process according to the present invention, it is possible to add perfluoroalkanoic anhydride or substrate to a mixture of the other reagents. However, it is preferred to add the inorganic peroxygen compound to a mixture of substrate and perfluoroalkanoic anhydride because this reduces the ratio of peroxygen to organic compounds at any given point in the addition. The inorganic peroxygen can be added in a single increment, but in order to employ a low ratio of peroxygen compound to organic compounds at any given point in the addition, it is often desirable to add the inorganic peroxygen compound over an addition period, either incrementally at intervals over the addition period, or continuously. Addition of the inorganic peroxygen compound over an addition period can also be advantageous when the inorganic peroxygen compound comprises sodium percarbonate, because addition over a period allows some control of any effervescence which may occur. The addition period can be varied widely at the discretion of the process user, but in many embodiments of the present invention, the addition period is selected in the range of from 5 minutes to several hours, such as up to 4 hours, particularly from 10 minutes to 2 hours. In certain embodiments of the present invention, the addition of the inorganic peroxygen compound can be carried out at a temperature different from the reaction temperature, usually a lower temperature, with the temperature being altered to the desired reaction temperature on completion of the addition.

The overall reaction period, including the period of introduction of the inorganic peroxygen compound, often comprises from about 2 to about 12 hours, and in many instances is from about 3 to about 8 hours. However, longer reaction periods of for example 12 to 30 hours can be employed, if desired by the user. On completion of the desired reaction period, the product can be separated from the reaction mixture without allowing any cooling of the reaction medium. However, in many embodiments the reaction can be terminated by allowing the reaction mixture to cool, usually to ambient temperature, or alternatively, the reaction mixture can be rapidly cooled by the application of cooling.

The product of the process according to the present invention can be separated from the reaction medium by means appropriate to the physical form of the product. For example, when the product is a solid, the product can be obtained by, for example, filtration or centrifugation. When the product is a liquid or is present as a solution in the reaction medium, the product can be obtained by solvent extraction, optionally followed by drying and evaporation of the extraction solvent. If desired, the extraction solvent can be recycled and employed in subsequent extractions. An alternative method of separating the product from the reaction medium when the product is a liquid comprises distillation, optionally under reduced pressure, including steam distillation.

The process according to the present invention can be carried out under irradiation, particularly ultraviolet radiation, which may in certain embodiments assist in the formation of free radicals.

According to one preferred aspect of the present invention, there is provided a one pot process for trifluoromethylation of a substrate selected from the group consisting of alkylbenzenes, halogenated aromatic compounds, alkoxybenzenes, arylbenzenes, and aromatic and aliphatic disulphides, characterised in that the process comprises contacting the substrate with trifluoroacetic anhydride in the presence of sodium percarbonate at a temperature greater than 40° C.

The trifluoromethylation process according to the present invention advantageously employs a mole ratio of trifluoroacetic anhydride to sodium percarbonate of greater than 3:1, and particularly from 6:1 to 10:1.

According to a second preferred aspect of the present invention, there is provided a one pot process for trifluoroacetoxylation of a substrate selected from the group consisting of alkylbenzenes and alkoxybenzenes, characterised in that the process comprises contacting the substrate with trifluoroacetic anhydride in the presence of sodium percarbonate at a temperature less than 35° C.

Having described the invention in general terms, specific embodiments thereof are described in greater detail by way of example only. In the Examples, all yields are quoted based on the available oxygen (Avox)employed.

EXAMPLE 1

To a 100 ml 3 necked-flask fitted with a condenser was added trifluoroacetic acid ("TFAA", 4.28 g, 0.02 mol) and toluene (10 ml, 0.09 mol). The mixture was heated to 50° C. and then sodium percarbonate ("PCS", 0.6 g, Avox 13.65%, 0.005 mol $H_2O_2$) was added over 10 minutes. On completion of the PCS addition, the reaction mixture was heated to 70° C. and maintained at that temperature for 4 hours. The reaction mixture was then allowed to cool to ambient temperature. The reaction was then worked up. Dichloromethane (30 ml) and biphenyl (as internal standard for gas chromatography, 0.15 g) were added, followed by aqueous sodium hydroxide solution (3% w/w, 20 ml). The mixture was stirred for 30 minutes, and the dichloromethane layer separated off. The dichloromethane layer was washed with two 20 ml aliquots of demineralised water and then dried over $MgSO_4$. The $MgSO_4$ was filtered off and the dichloromethane layer analysed by gas chromatography, gas chromatography-mass spectrometry and $^{19}F$ NMR.

The yield of trifluoromethylated products was 55.7%, including 4-methylbenzotrifluoride (15.1%), 3-methylbenzotrifluoride (11.2%)and 2-methylbenzotrifluoride (29.4%). The yield of trifluoroacetoxylated products was 26.2%.

EXAMPLE 2

The method of Example 1 was followed, except that 40 g toluene (0.43 mol) and 42 g TFAA (0.2 mol), 6 g PCS (0.05 mol $H_2O_2$) added over 30 minutes were employed, and the reaction mixture was heated to 55° C. The work up was as described in Example 1, except that 100 ml dichloromethane and 1.2 g biphenyl was employed.

The yield of trifluoromethylated products was 40%, including 4-methylbenzotrifluoride (10.8%), 3-methylbenzotrifluoride (8.0%)and 2-methylbenzotrifluoride (21.2%). The yield of trifluoroacetoxylated products was 18%.

This result demonstrated that the process of Example 1 could successfully be employed on a larger scale.

EXAMPLE 3

The method of Example 1 was employed, except that TFAA (4.28 g, 0.02 mol) was added to a mixture of toluene (10 ml, 0.09 mol) and PCS (0.6 g, 0.005 mol $H_2O_2$) at a temperature of 50° C. over a 10 minute addition period.

The yield of trifluoromethylated products was 40.2%, including 4-methylbenzotrifluoride (10.9%), 3-methylbenzotrifluoride (8.0%) and 2-methylbenzotrifluoride (21.3%). The yield of trifluoroacetoxylated products was 20.1%.

This result demonstrated that the perfluoroalkanoic anhydride could successfully be added to a mixture of substrate and inorganic peroxygen compound.

EXAMPLE 4

The method of Example 1 was followed, except that 8.56 g TFAA (0.04 mol) was employed, and that the reaction temperature was 55° C.

The yield of trifluoromethylated products was 80%, including 4-methylbenzotrifluoride (21.6%), 3-methylbenzotrifluoride (16.0%) and 2-methylbenzotrifluoride (42.4%). The yield of trifluoroacetoxylated products was 19%.

This result demonstrated that the yield of trifluoroalkylated product could be achieved by increasing the mole ratio of perfluoroalkanoic anhydride to inorganic peroxygen compound from 4:1 to 8:1.

EXAMPLE 5

The method of Example 1 was followed, except that 10 ml anisole (0.09 mol) was employed in place of the toluene.

The yield of trifluoromethylated products was 43.5%, including 4-methoxybenzotrifluoride (10.9%), 3-methoxybenzotrifluoride (7.2%) and 2-methoxybenzotrifluoride (25.4%). No trifluoroacetoxylated products were detected.

This result demonstrated that anisole could be perfluoroalkylated by the process of the present invention, but that under these conditions, no perfluoroacyloxylation occurred.

EXAMPLE 6

The method of Example 1 was followed, except that 10 ml bromobenzene (0.095 mol) was employed in place of the toluene.

The yield of trifluoromethylated products was 34.6%, including 4-bromobenzotrifluoride (10.3%), 3-bromobenzotrifluoride (7.4%) and 2-bromobenzotrifluoride (16.9%). No trifluoroacetoxylated products were detected.

This result demonstrated that bromobenzene could be perfluoroalkylated by the process of the present invention, but that under these conditions, no perfluoroacyloxylation occurred.

EXAMPLE 7

The method of Example 6 was followed except that 8.56 g TFAA (0.04 mol) was employed.

The yield of trifluoromethylated products was 53.5%, including 4-bromobenzotrifluoride (14.8%), 3-bromobenzotrifluoride (12.3%) and 2-bromobenzotrifluoride (26.4%). No trifluoroacetoxylated products were detected.

This result demonstrated that increasing the mole ratio of perfluoroalkanoic anhydride to inorganic peroxygen compound from 4:1 to 8:1 increased the yield of perfluoroalkylated product when bromobenzene was the substrate.

EXAMPLE 8

0.6 g PCS (0.005 mol $H_2O_2$) was charged to a 100 ml round-bottomed flask, and cooled to 0°–5° C. in an ice water bath. TFAA (4.28 g, 0.02 mol) was added over 10 minutes, and the mixture stirred for 1 hour with the temperature maintained at 0°–5° C. To this mixture was added 10 ml toluene (0.09 mol) over 15 minutes, and the mixture heated to 70° C. After 4 hours at 70° C., the reaction mixture was allowed to cool to ambient temperature, and the reaction worked up by the same method as for Example 1.

The yield of trifluoromethylated products was 40.4%, including 4-methylbenzotrifluoride (11.1%), 3-methylbenzotrifluoride (7.3%) and 2-methylbenzotrifluoride (22.0%). The yield of trifluoroacetoxylated products was 40.4%.

This result demonstrated that the substrate could successfully be added to a mixture of perfluoroalkanoic anhydride and inorganic peroxygen compound in the process according to the instant invention.

EXAMPLE 9

The method of Example 8 was followed except that 1,4-dimethylbenzene (10 ml, 0.08 mol) was employed in place of the toluene.

The yield of 2,4-dimethylbenzotrifluoride was 43.4%. The yield of trifluoroacetoxylated products was 43.4%.

This result demonstrated that the process according to the present invention could be applied to 1,4-dimethylbenzene as a substrate.

EXAMPLE 10

The method of Example 8 was followed except that chlorobenzene (10 ml, 0.098 mol) was employed in place of the toluene.

The yield of trifluoromethylated products was 28.9%, including 4-chlorobenzotrifluoride (8.7%) and 2-chlorobenzotrifluoride (20.2%). No trifluoroacetoxylated products were detected.

This result demonstrated that chlorobenzene could be perfluoroalkylated by the process of the present invention, but that under these conditions, no perfluoroacyloxylation occurred.

EXAMPLE 11

The method of Example 8 was followed except that biphenyl (5 g, 0.03 mol) was employed in place of the toluene.

The yield of trifluoromethylated products was 16.4% 4-trifluoromethylbiphenyl, with trace amounts of di-trifluoromethylbiphenyls. No trifluoroacetoxylated products were detected.

This result demonstrated that biphenyl could be perfluoroalkylated by the process of the present invention, but that under these conditions, no perfluoroacyloxylation occurred.

EXAMPLE 12

The method of Example 1 was followed, except that sodium perborate monohydrate (0.55 g, 0.005 mol available oxygen) was employed in place of the sodium percarbonate.

The yield of trifluoromethylated products was 23.3%, including 4-methylbenzotrifluoride (6.3%), 3-methylbenzotrifluoride (4.7%) and 2-methylbenzotrifluoride (12.3%). The yield of trifluoroacetoxylated products was 21.7%.

This result demonstrated that sodium perborate monohydrate could be employed as inorganic peroxygen compound in the process according to the present invention.

EXAMPLE 13

The method of Example 1 was followed, except that calcium peroxide (0.46 g, 0.005 mol available oxygen) was employed in place of the sodium percarbonate.

The yield of trifluoromethylated products was 15.7%, including 4-methylbenzotrifluoride (4.2%), 3-methylbenzotrifluoride (3.2%) and 2-methylbenzotrifluoride (8.3%). The yield of trifluoroacetoxylated products was 23.5%.

This result demonstrated that calcium peroxide could be employed as inorganic peroxygen compound in the process according to the present invention, and that under these conditions favoured increased perfluoroacyloxylation relative to perfluoroalkylation.

EXAMPLE 14

The method of Example 1 was followed, except that 0.2 g 85% w/w aqueous hydrogen peroxide solution and 0.6 g sodium carbonate were employed in place of the sodium percarbonate.

The yield of trifluoromethylated products was 15.9%, including 4-methylbenzotrifluoride (4.3%), 3-methylbenzotrifluoride (3.2%) and 2-methylbenzotrifluoride (8.4%). The yield of trifluoroacetoxylated products was 26.9%.

This result demonstrated that a mixture of concentrated aqueous hydrogen peroxide solution and sodium carbonate could be employed as inorganic peroxygen compound in the process according to the present invention, and that under these conditions favoured increased perfluoroacyloxylation relative to perfluoroalkylation.

EXAMPLE 15

The method of Example 4 was followed, except that phenyldisulphide (5 g, 0.023 mol) was employed in place of the toluene.

The yield of trifluoromethylthiobenzene was 13%. No trifluoroacetoxylated products were detected.

This result demonstrated that disulphides could be perfluoroalkylated by the process according to the present invention.

EXAMPLES 16 TO 20

The method of Example 1 was repeated, with the temperature of the reaction being varied as detailed below. The % yields of trifluoromethylated (Yield $CF_3$) and trifluoroacetoxylated (Yield $OCOCF_3$) products are given below.

| Example number | Temperature °C. | Yield $CF_3$ | Yield $OCOCF_3$ |
|---|---|---|---|
| 16 | 20 | 0 | 61 |
| 17 | 30 | 10 | 47 |
| 18 | 40 | 25 | 36 |
| 19 | 60 | 45 | 30 |
| 20 | 70 | 56 | 25 |

These results demonstrated that the nature of the perfluoro substitution achieved by the process according to the present invention can be varied by control of the process temperature.

EXAMPLE 21

The method of Example 5 was followed, except that the reaction was carried out at room temperature for a period of 18 hours.

The yield of trifluoromethylated products was 33%, including 4-methoxybenzotrifluoride (8.3%), 3-methoxybenzotrifluoride (5.5%) and 2-methoxybenzotrifluoride (19.1%). The yield of trifluoroacetoxylated products was 26.2%.

This result, when compared with that for Example 5, again demonstrated that by selection of a lower reaction temperature, the nature of the substitution could be influenced in favour of increased perfluoroacyloxylation.

Comparison 22

The method of Example 1 was followed, except that trifluoromethanesulphonic anhydride (5.64 ml, 0.02 mol) was employed in place of the TFAA. No trifluoromethylated products were observed.

Comparison 23

The method of Example 1 was followed, except that trifluoromethanesulphonic acid (3.0 ml, 0.02 mol) was employed in place of the TFAA. No trifluoromethylated products were observed.

The results of Examples 1 to 21 demonstrate that the process according to the instant invention can be employed to trifluoromethylate a number of different substrates under a range of different conditions, and employing differing sources of inorganic peroxygen compounds. The results of Comparisons 22 and 23 (not according to the present invention), where no perfluoroalkylation occurred demonstrate the importance of the selection of a perfluoroalkanoic anhydride instead of an alternative a perfluoroalkyl group.

We claim:

1. In a process for introducing a perfluorinated substituent into an organic substrate susceptible to electrophilic attack, the improvement wherein the process comprises contacting a substrate in a one pot process with a perfluoroalkanoic anhydride in the presence of an inorganic peroxygen compound at a temperature of greater than 10° C., the substrate being free from any heteroatom bonded to a hydrogen atom, and being selected from the group consisting of aromatic compounds comprising a hydrogen atom bonded to an aromatic ring and/or at least two concatenated nucleophilic heteroatoms, and aliphatic compounds comprising at least two concatenated nucleophilic heteroatoms.

2. A one pot process according to claim 1, characterised in that the inorganic peroxygen compound is selected from the group consisting of sodium percarbonate, sodium perborate mono and tetrahydrates, calcium peroxide, potassium monopersulphate, aqueous hydrogen peroxide solution and mixtures of aqueous hydrogen peroxide solution with sodium carbonate or borax.

3. A process according to claim 2, characterised in that the inorganic peroxygen compound is sodium percarbonate.

4. In a process for the perfluoroalkylation of an organic substrate susceptible to electrophilic attack, the improvement wherein the process comprises contacting a substrate in a one pot process with a perfluoroalkanoic anhydride in the presence of sodium percarbonate at a temperature greater than 45° C., the substrate being free from any heteroatom bonded to a hydrogen atom, and being selected from the group consisting of aromatic compounds comprising a hydrogen atom bonded to an aromatic ring and/or at least two concatenated nucleophilic heteroatoms, and aliphatic compounds comprising at least two concatenated nucleophilic heteroatoms.

5. A process according to any one preceding claim, characterised in that the substrate has a vapour phase Ionisation Potential of less than 9.5 electron volts.

6. A process according to any one of claims 1 to 4, characterised in that the substrate is selected from the group consisting of alkyl, aryl, halogen and alkoxy substituted aromatic compounds, and aromatic and aliphatic disulphides.

7. A process according to claim 6, characterised in that the substrate is selected from the group consisting of toluene, ethylbenzene, xylene, chlorobenzene, bromobenzene, biphenyl, anisole and diphenyldisulphide.

8. A process according to any one of claims 1 to 4, characterised in that the perfluoroalkanoic anhydride comprises trifluoroacetic anhydride.

9. A process according to any one of claim 1 to 4, characterised in that the mole ratio of perfluoroalkanoic anhydride to inorganic peroxygen compound is from 2:1 to 10:1.

10. In a process for trifluoromethylation of a substrate selected from the group consisting of alkylbenzenes, halogenated aromatic compounds, alkoxybenzenes, arylbenzenes, and aromatic and aliphatic disulphides, the improvement wherein the process comprises contacting the substrate in a one pot process with trifluoroacetic anhydride in the presence of sodium percarbonate at a temperature greater than 40° C.

11. A process according to claim 10, characterised in that the mole ratio of trifluoroacetic anhydride to sodium percarbonate is greater than 3:1.

12. In a process for trifluoroacetoxylation of a substrate selected from the group consisting of alkylbenzenes and alkoxybenzenes, the improvement wherein the process comprises contacting the substrate in a one pot process with trifluoroacetic anhydride in the presence of sodium percarbonate at a temperature less than 35° C.

13. A process according to any one of claims 1 to 4 or 10 to 12, characterised in that the substrate serves as solvent.

14. A process according to claim 5, characterised in that the substrate has a vapour phase Ionisation Potential of less than 9 electron volts.

15. A process according to claim 11, characterised in that the mole ratio of trifluoroacetic anhydride to sodium percarbonate is from 6:1 to 10:1.

* * * * *